United States Patent [19]

Hogan

[11] 4,452,439
[45] Jun. 5, 1984

[54] SAFETY LATCHES FOR TILTABLE EMERGENCY X-RAY EXAMINATION TABLE

[75] Inventor: William F. Hogan, Woodbury, N.J.

[73] Assignee: Spectrum X-Ray Corporation, Westville, N.J.

[21] Appl. No.: 369,354

[22] Filed: Apr. 19, 1982

[51] Int. Cl.³ .............................................. G03B 41/16
[52] U.S. Cl. ................................. 269/323; 378/209; 74/527
[58] Field of Search ..................... 108/143, 6; 5/82 R, 5/81 B, 62; 74/527, 540, 529; 269/322–326; 378/209

[56] References Cited

U.S. PATENT DOCUMENTS

| | | | |
|---|---|---|---|
| 2,936,652 | 5/1960 | Gunzner | 74/527 |
| 3,323,601 | 6/1967 | Vebel | 74/527 |
| 3,643,604 | 2/1972 | Jones et al. | 108/143 |
| 3,840,221 | 10/1974 | Hogan | 378/209 |
| 4,131,801 | 12/1978 | Hogan | 378/209 |
| 4,156,815 | 5/1979 | Hogan | 378/209 |

Primary Examiner—Robert C. Watson
Attorney, Agent, or Firm—Paul & Paul

[57] ABSTRACT

An emergency X-ray examination table has a top assembly comprising a primary top and a secondary top which is slidable on the primary top in the lengthwise direction of the table. The patient lies on the slidable top which is extendible beyond the limits of the primary top so that the head of the patient may be closely examined. The table top assembly is tiltable along a transverse axis. A latching mechanism prevents the secondary top from sliding downwardly when the table top assembly is tilted. A locking mechanism prevents the table top assembly from being tilted unless the latching mechanism has been placed in latched position. Another locking mechanism prevents the latching mechanism from being actuated unless the slidable top is in a position to be latched.

9 Claims, 7 Drawing Figures

SAFETY LATCHES FOR TILTABLE EMERGENCY X-RAY EXAMINATION TABLE

BACKGROUND OF THE INVENTION

This invention relates to X-ray examination tables and particularly to X-ray examination tables intended for emergency use as, for example, in transporting a patient from the emergency station of a hospital to an X-ray examining room. Such an X-ray examination table is usually mounted on a base pedestal which is supported on a carriage which usually has four pivotal wheels for allowing movement of the carriage in any direction.

The present invention relates particularly to an X-ray examination table of the above type which includes a flat top assembly which is movable elevationally, and lengthwise, and also transversely, relative to the table base. The flat top assembly comprises a primary top and a secondary top which is slidable in the lengthwise direction on the primary top. The patient lies on the secondary slidable top. Such top has a narrow head area which when positioned out beyond the primary top allows for close neuro examination of the head of the patient.

The present invention relates to an emergency X-ray examination table of the above type in which the table top assembly is tiltable so that the head of the patient may not only be extended beyond the underlying primary table top, but so that the patient's head may be raised or lowered from the horizontal position, as desired by the examining doctor.

In an emergency situation, when a patient in shock is placed on an X-ray examination table of the foregoing type, the doctor may order that the head of the patient be lowered so as to cause blood to flow to the patient's head. When this is done, the slidable top carrying the weight of the patient may continue to slide in the inclined downwardly direction and the patient may be injured.

An X-ray examination table with a tiltable table top is shown in my U.S. Pat. No. 4,131,801 issued Dec. 26, 1978, and also in my U.S. Pat. No. 4,156,815 issued May 29, 1979. However, neither of these patents involves a slidable table top.

An X-ray examination table having a slidable top is shown in my U.S. Pat. No. 3,840,221 issued Oct. 8, 1974 but the table top in that patent is not tiltable.

SUMMARY OF THE INVENTION

A principal object of the present invention is to provide, in an emergency X-ray examination table having a slidable tiltable table top, manually operable means for latching the table top against sliding movement when the table top is in a tilted position.

Another object of the present invention is to provide an emergency X-ray examination table having a slidable tiltable top which has means for preventing tilting of the top unless the slidable top is latched against sliding movement.

Another object is to provide a latching mechanism for a tiltable slidable X-ray examination table top which, once placed in the latched position, remains locked in that position until the table top is returned from the tilted to the horizontal position.

Another object is to provide means for locking the manually operable latch means against actuation unless the slidable table top is in a position to be latched.

DETAILED DESCRIPTION OF THE PREFERRED EMBODIMENTS

Figure 1:
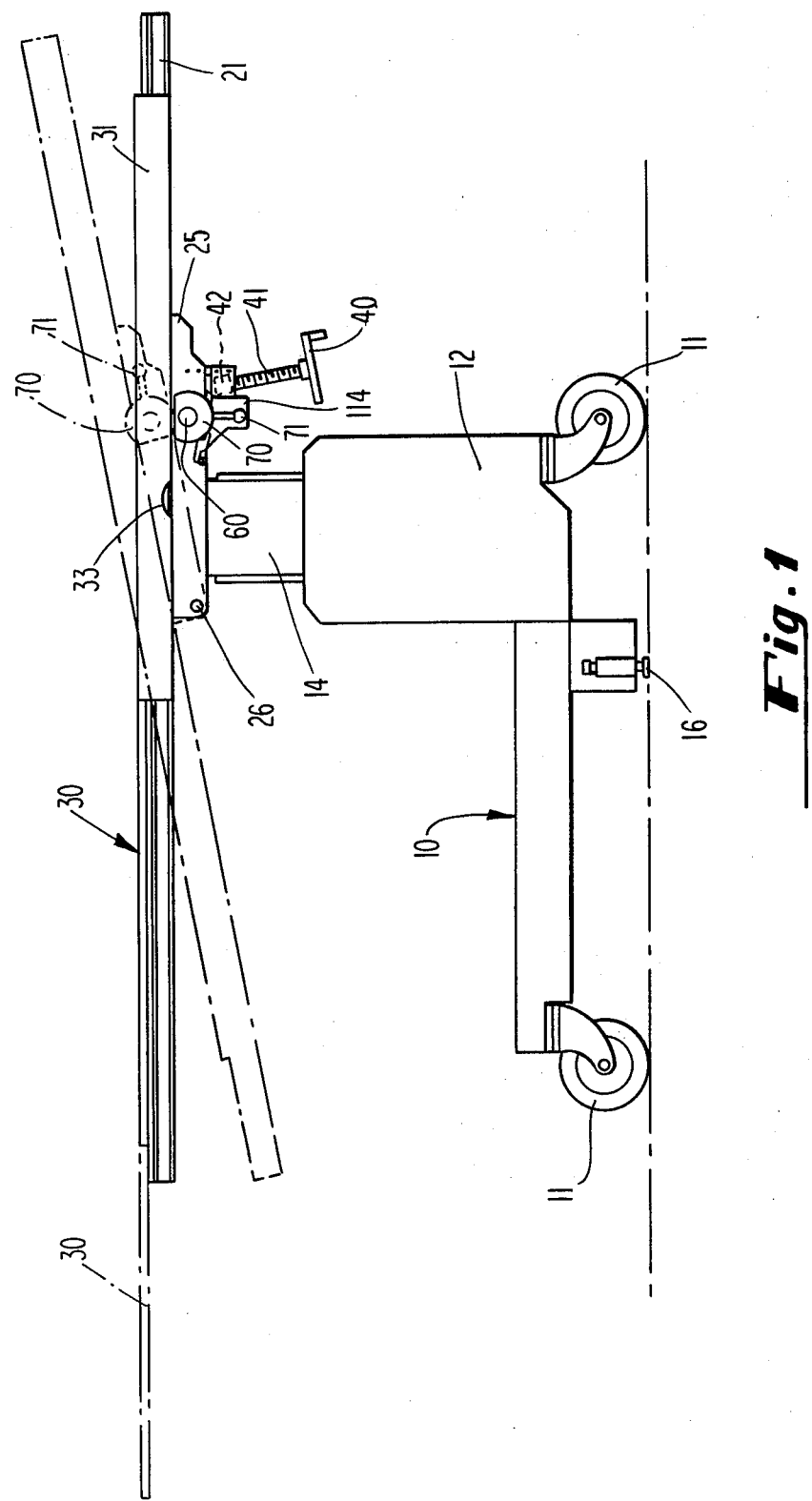
FIG. 1 is a side elevational view of an emergency X-ray examination table having a latching mechanism in accordance with the present invention.

In FIG. 1, the emergency X-ray examination table is mounted on a carriage 10 which is movable in any direction by means of four wheels 11 each of which is independently pivotal. The carriage may be clamped to the floor by a foot clamp 16. Supported on carriage 10 is a base pedestal 12, and within pedestal 12 is an elevator mechanism 14. Mounted on the upper structure 114 of elevator 14 is a table top assembly comprising a primary top 20 on which a second top 30 is slidingly movable in the lengthwise directions. In FIG. 1, the left end is the head end. This end of the slidable top 30 may be narrow and extendible beyond the primary top 20 to permit close examination of the head of the patient.

Figure 5:
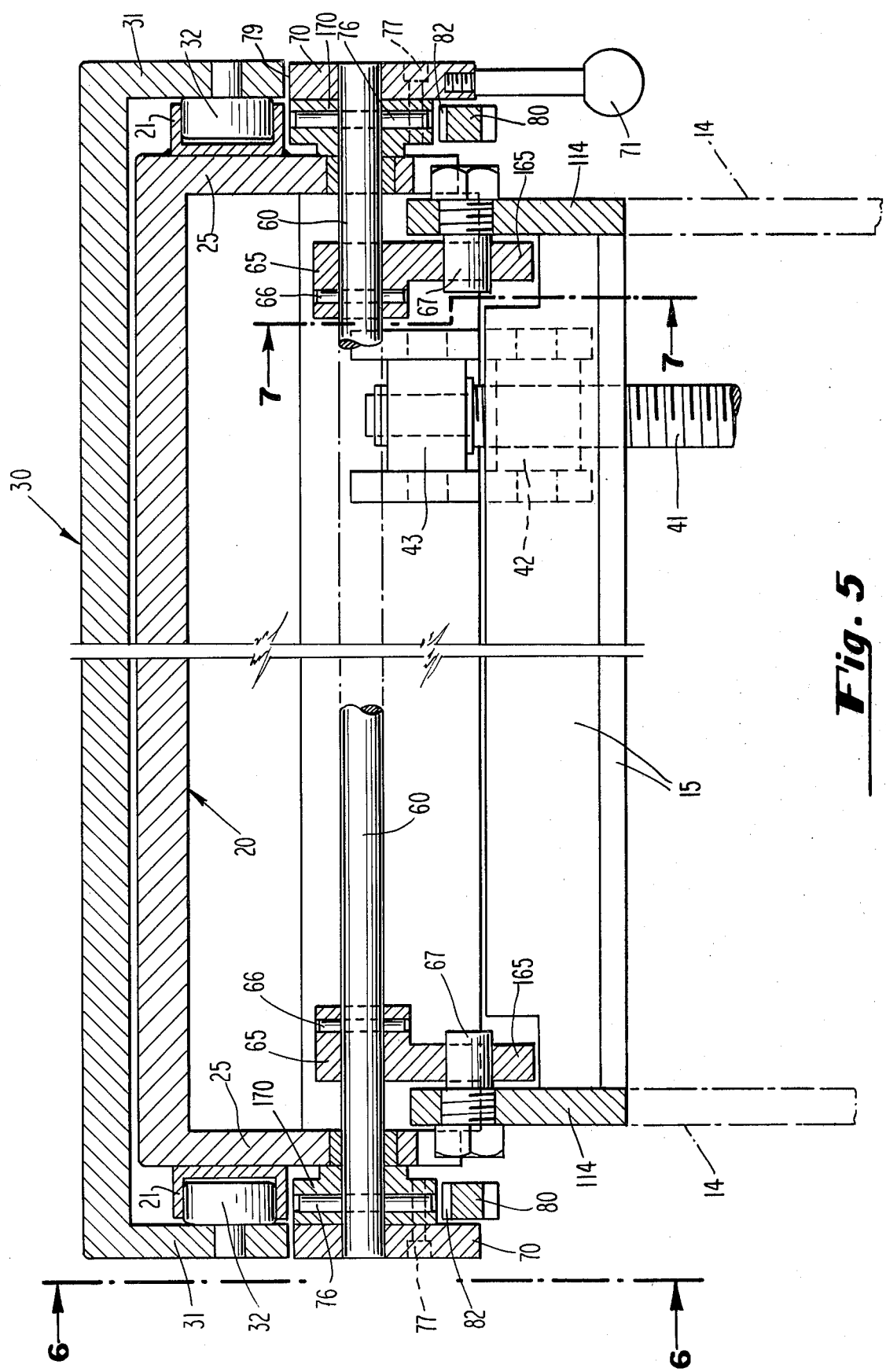
FIG. 5 is an elevational view, in section, along the line 5—5 of FIG. 2.

As best seen in FIG. 5, slidable top 30 is channel shaped having a downwardly extending flange 31 on each lengthwise side. Mounted on each flange 31 are rollers 32 which ride in a channel 21 secured to the depending sidewall 25 of the table top 20. The rollers 32 carry the slidable top 30 as it is moved back and forth relative to the primary top 20.

As seen in FIG. 5, the various components on each side of the table top assembly are similar. That is, the components on one side of the table have counterparts on the other side. In the following description, the component on one side of the table and its counterpart on the other side are identified by the same reference numerals. Since the two sides of the table are very similar, only one side will be described in the description which follows.

There are two exceptions to what has just been said about the components on one side of the table top having a counterpart on the other. Stated briefly, while the latching mechanism on one side of the table top has its counterpart on the other, the manually operable control lever 71 for the latching mechanism is provided on only one side of the table. Also, a spring-biased locking plunger 90 for the latching mechanism is provided on only one side of the table.

Figure 2:
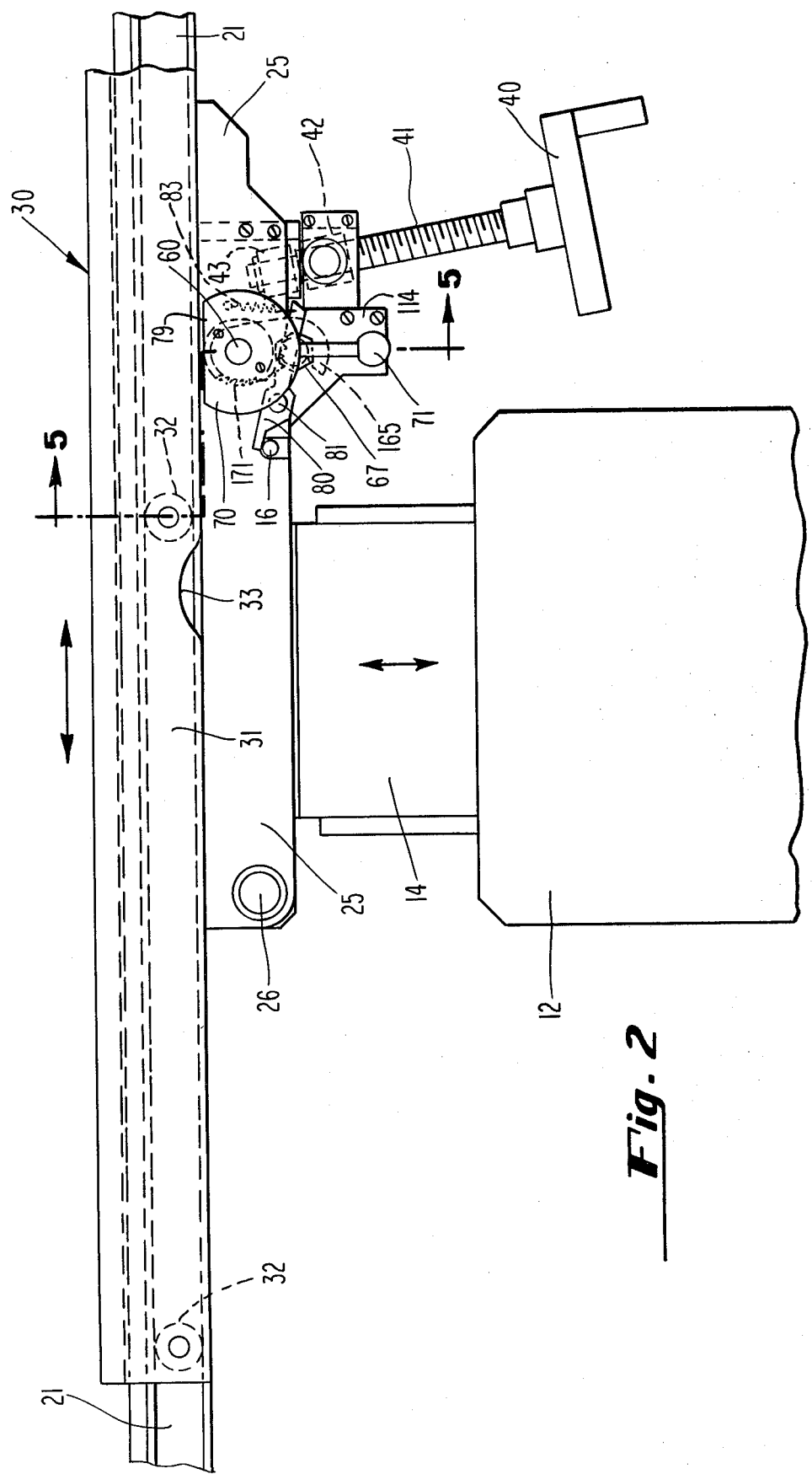
FIG. 2 is a side elevational view of a portion of the table of FIG. 1, showing the latching mechanism.
Figure 3:
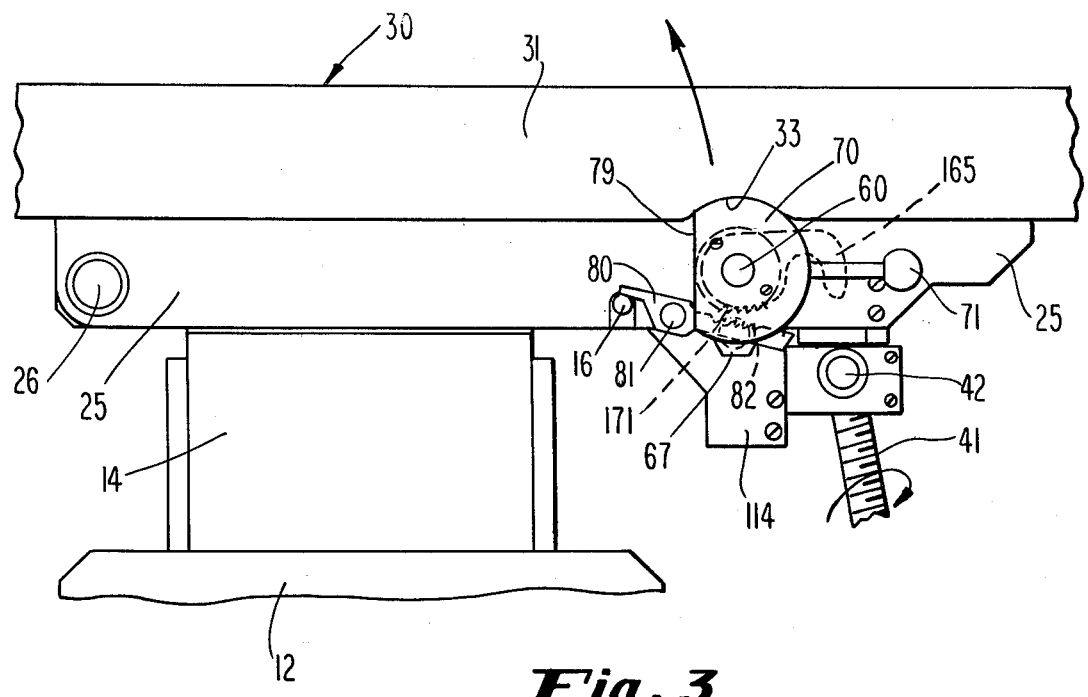
FIG. 3 is a side elevational view showing the latch of the present invention latching the slidable table top when the table top assembly is in horizontal position, before it is tilted.
Figure 4:
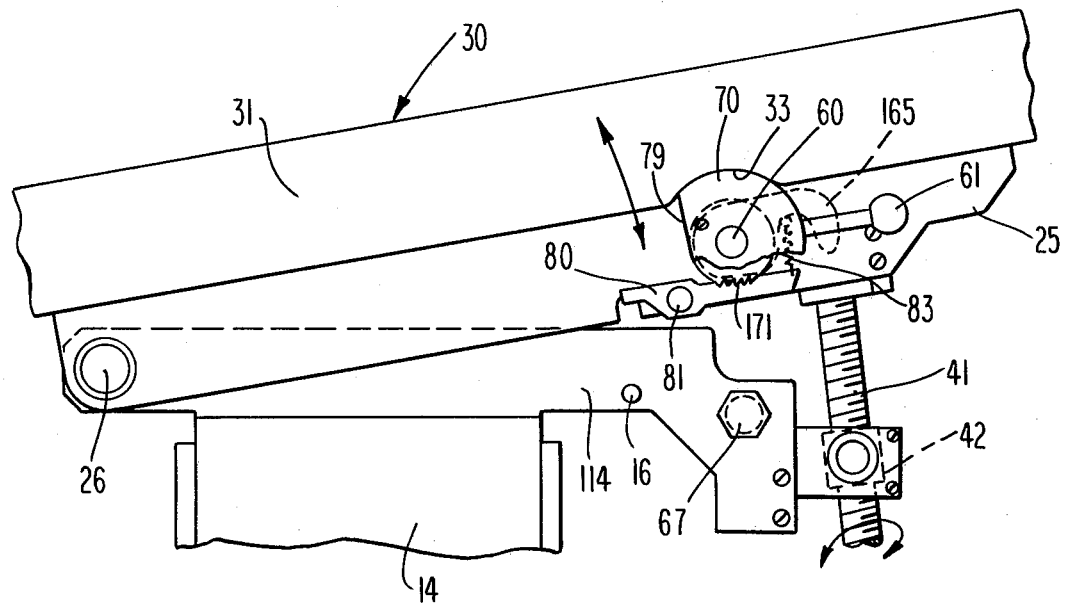
FIG. 4 is a side elevational view similar to that of FIG. 3 but showing the latched table top assembly in tilted position.

Referring now to FIGS. 1-4, the table top assembly, comprising the primary table top 20 and the slidable table top 30, is tiltable by means of a manual crank 40 and screw 41. Screw 41 is threaded in a nut 42 which is fixed to a cross-support 15 (FIG. 5) of the elevator 14 so that when screw 41 is rotated by crank 40, screw 41 moves upwardly carrying with it the table top assembly. The left end of the sidewall 25, as viewed in FIGS. 1 and 2, is supported for pivotal movement on a pivot pin 26. Thus, when the screw 41 is rotated to move the screw upwardly through the fixed nut 42, the right end of the table top is pivotally lifted, as illustrated in FIG. 4 and as shown in phantom in FIG. 1.

Unless means are provided for latching the slidable table top 30 against free sliding movement, there is danger, when the table top assembly is tilted, that the slidable table top 30 will continue to slide downwardly at the inclined angle at which the table top is tilted. This is particularly true when the weight of a patient is on the slidable table top.

The danger referred to above is avoided, in accordance with the present invention, by the provision of latch means for latching the table top 30 against sliding movement and by the provision of lock means for locking the table top against being tilted by the crank 40 unless the table top 30 is latched against sliding.

The latch means against sliding comprises a generally circular but truncated disc 70 having a flat 79. Disc 70 is mounted on a cross shaft 60 (FIG. 5) in such position that the flat 79 of the disc is parallel with and slightly below the lower edge of flange 31 of the slidable table top 30.

Flange 31 is provided with a recess 33 which is preferably of a size and shape corresponding to that of the segment which is missing from disc 70. Because disc 70 is so positioned on shaft 60 that the flat 79 is immediately below the under surface of flange 31 of slidable table top 30, disc 70 cannot be moved rotationally on shaft 60 unless recess 33 is in alignment with disc 70, so long as the underface of flange 31 is just above the flat 79. This occurs at only one position of the table top assembly. Thus, to latch the slidable top 30 against sliding movement, the table top assembly must be pulled to such position that recess 33 is in registry with disc 70.

Also mounted on cross shaft 60 and pinned to cross shaft 60 by a pin 66 (FIG. 5) is a member 65 having a hook end 165. When latching disc 70 is in the position shown in FIGS. 1 and 2 in which the flat 79 of the disc 70 is adjacent to the undersurface of flange 31 of slidable top 30, the hook portion 165 of the hook member 65 embraces a stud 67 which is fixed in the upper structure 114 of elevator 14, as seen in FIG. 5. As a result of the hook mechanism just described, if locking disc 70 and recess 33 are not in alignment with each other, the tilt crank 40 cannot be rotated by the operator to tilt the table top because the table top is locked by hook 165 to the elevator 14.

Once control lever 71 has been turned 90 degrees counterclockwise, as viewed in FIGS. 1-4, to cause a segment of disc 70 to enter and occupy recess 33 in the slidable table top 30, and after crank 40 has been rotated to start lifting the table top assembly, there exists the possibility that locking disc 70 may be dislodged from recess 33, as by accidental or otherwise movement of control lever 71 in the counterclockwise direction. To guard against this possibility, means are provided by the present invention for automatically locking latching disc 70 in the latching position as soon as the table top assembly, in response to the turning of lift crank 40, starts rising from the horizontal position.

As shown in FIGS. 1-5, and best seen in FIG. 5, adjacent disc 70, and pinned thereto as by pin 77, is a disc 170 having a diameter corresponding to twice the radius of the flat portion 79 of latching disc 70. Disc 170 is pinned, as by pin 76, to shaft 60 and, accordingly, when latching disc 70 is moved rotationally by lever 71, disc 170 is moved rotationally to a corresponding extent. A portion of the peripheral surface of disc 170 is provided with teeth 171, as best seen in FIGS. 3-4.

Positioned just below disc 170 is a lever 80 mounted for pivotal movement on a pin 81 which is fixed in sidewall 25 of primary table top 20. The upper surface of lever 80 is provided with teeth 82. The right end of lever 80 is spring biased in the upward, or counterclockwise direction as viewed in FIGS. 3-4, by a biasing spring 83. So long as the table top assembly is in the horizontal position illustrated in FIG. 3, the left end of lever 80 remains in contact with a pin 16 which is fixed in upper structure 114 of elevator 14. Thus, pin 16 prevents counterclockwise rotational movement of lever 80. When, however, the table top assembly is lifted as illustrated in FIG. 4, and as soon as the left end of lever 80 clears the pin 16, lever 80 moves in a counterclockwise direction about pin 81 in response to the pull of biasing spring 83. When the lever 80 so moves, the teeth 82 of the lever come into interlocking engagement with the teeth 171 of disc 170. This interlocking engagement of the teeth 82, 171 prevents rotation of the latching disc 70.

One additional safety feature is provided in accordance with the present invention. As indicated in phantom in FIG. 1, the extent to which the slidable table top 30 is capable of being extended in the direction of the head of the table is such that the rearward end of flange 31 moves forwardly beyond the location of latching disc 70, thereby clearing the disc 70 for rotational movement. As a result, the possibility exists that when the sliding table top 30 is fully extended in the forward direction, the lever 71 may be used to rotate latching disc 70 in the counterclockwise direction, thereby unhooking hook 165 from pin 67 and making it possible for crank 40 to be rotated to tilt the table with the slidable table top 30 unlatched. This, of course, is undesirable.

Figure 6:
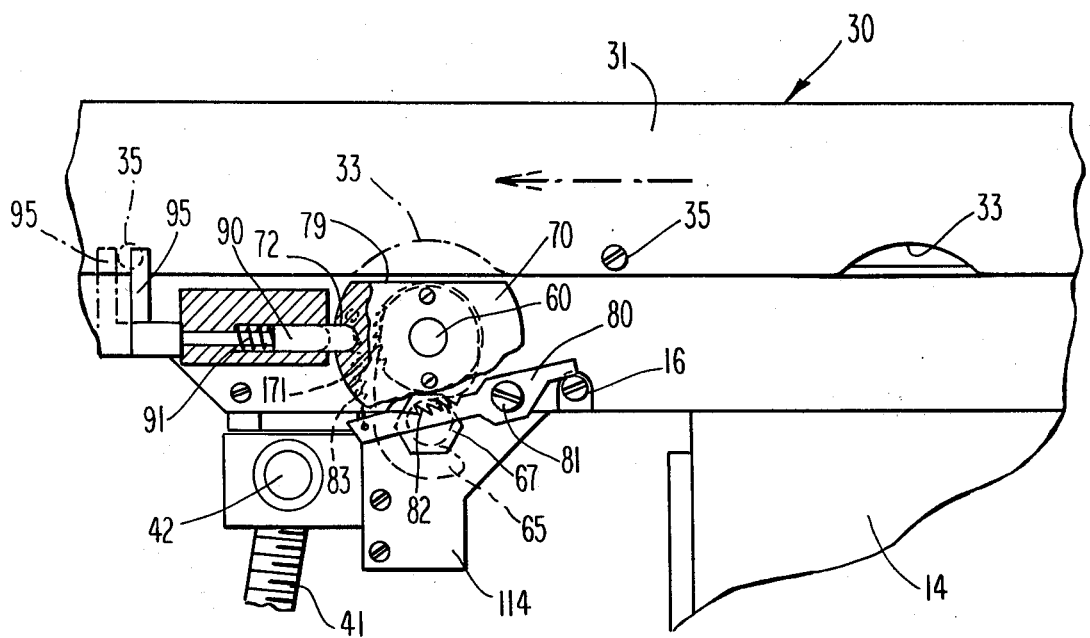
FIG. 6 is an elevational view showing the latch mechanism on the opposite side of the table from that shown in FIGS. 1-4, as viewed along line 6—6 of FIG. 5.
Figure 7:
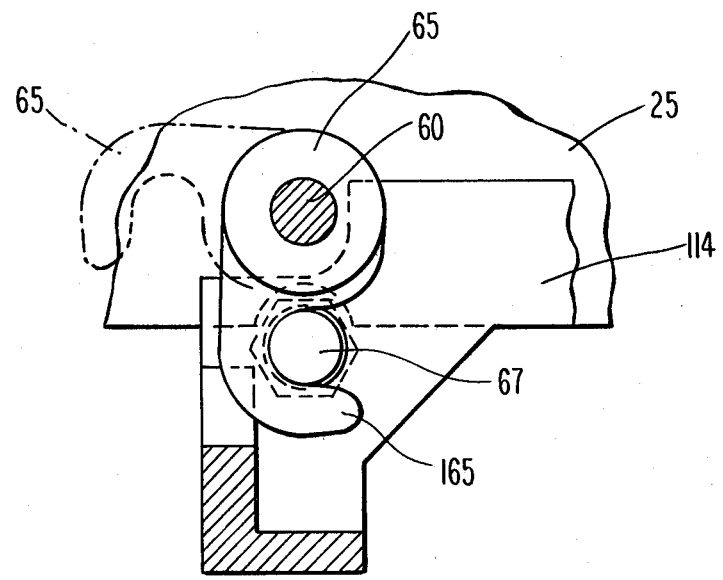
FIG. 7 is a detailed view of the hook which prevents the table top assembly from being tilted by the attendant when the latching mechanism is not latched, as seen looking along line 7—7 of FIG. 5.

To prevent rotation of latching disc 70 after the undersurface of flange 31 has passed beyond flat 79, a locking plunger 90 is provided on one side only of the table. Such a plunger 90 is illustrated in FIG. 6 of the drawing. As there shown, plunger 90 is spring biased by compression spring 91 such that the nose of the plunger 90 enters within a recess 72 in latching disc 70. So long as the nose of the plunger 90 is within the recess 72, the latching disc 70 cannot be moved rotationally.

In accordance with the present invention, the plunger 90 is unlatched automatically when the slidable table top 30 is pulled rearwardly for the purpose of placing recess 33 in alignment with latching disc 70. As viewed in FIG. 6, rearward movement of the slidable table top 30 is toward the left (not toward the right as in FIG. 1,2,3 and 4). As the slidable table top 30 is pulled rearwardly in the direction of the arrow in FIG. 6, just before recess 33 comes into registry with flat 72 of latching disc 70, a pin 35 on the flange 31 of the slidable top 30 comes into contact with handle 95 of the spring loaded plunger 90 and moves the plunger rearwardly from the position shown in solid line in FIG. 6 to the position shown in phantom, thereby withdrawing the nose of plunger 90 from hole 72 and releasing latching disc 70 for rotational movement.

What is claimed is:

1. In an X-ray examination table having a table top which is slidable on a non-slidable top, both of which are tiltable about the transverse axis of the table, said slidable top having side flanges, the improvement which comprises the provision of means for latching the slidable table top against unwanted sliding movement when the table tops are tilted, said latching means comprising:
   a. a generally circular truncated disc having a flat;
   b. means mounting said disc in such position that its flat is immediately adjacent and below the undersurface of a side flange of said slidable table top;
   c. a recess in said side flange;
   d. means for moving said disc rotationally to cause a segment of said disc to enter into said recess; and
   e. first locking means for locking said disc in the last-named position;

2. Apparatus according to claim 1 wherein second locking means are provided for locking said disc against rotation unless said recess is in alignment with said disc.

3. Apparatus according to claim 1 wherein said first locking means comprises:
   a. a second disc coaxially adjacent and connected to said truncated disc, said second disc having a diameter corresponding to twice the radius of the flat portion of said disc;
   b. first teeth on the peripheral surface of said second disc;
   c. a locking lever mounted for pivotal movement in the vertical plane on the non-slidable tiltable portion of the table top;
   d. second teeth on an edge of said locking lever;
   e. biasing means tending to move said locking lever pivotally to cause said first and second teeth to come into interlocking engagement;
   f. means mounted on a non-tiltable portion of said table for preventing pivotal movement of said biased locking lever when said table tops are in non-tilted position and for allowing pivotal movement of said lever when said table tops are in tilted position.

4. Apparatus according to claim 3 wherein second locking means are provided for locking said disc against rotation unless said recess is in alignment with said disc.

5. In an X-ray examination table having a base and a table top which is slidable on a non-slidable top both of which are tiltable about the transverse axis of the table, said slidable top having side flanges, the improvement which comprises the provision of means for latching the slidable table top against unwanted sliding movement when the table tops are tilted, said latching means comprising:
   a. a recess in the side flange of the said slidable table top;
   b. a latch member mounted on said non-slidable table top and insertable into said recess;
   c. manually operable means for inserting said latch member into said recess;
   d. first locking means for locking said latch member in said recess when said slidable table top is in tilted position; and
   e. means for preventing tilting of said table top except when said latch member is in said recess.

6. Apparatus according to claim 5 wherein second locking means are provided for locking said latch member in non-latched position except when said recess is in a position to receive said latch member.

7. Apparatus according to claim 5 wherein said latch member is a rotatable truncated disc having a flat.

8. Apparatus according to claim 7 wherein said first locking means comprises first and second toothed members mounted on said non-slidable top, each having teeth adapted to interlock with the teeth of the other, one of said toothed members being rotatable with said disc, the other of said toothed members being a lever spring-biased toward interlocking engagement.

9. Apparatus according to claim 8 wherein said means for preventing tilting of said table comprises a hook member rotatable with said disc, and a pin fixed in the base of said table adapted to be embraced by said hook.

* * * * *